United States Patent [19]

Smolanoff

[11] Patent Number: 4,466,967
[45] Date of Patent: * Aug. 21, 1984

[54] ARTHROPOD REPELLENTS

[75] Inventor: Joel R. Smolanoff, Chalfont, Pa.

[73] Assignee: Rohm and Haas Company, Philadelphia, Pa.

[ * ] Notice: The portion of the term of this patent subsequent to Dec. 6, 2000 has been disclaimed.

[21] Appl. No.: 402,182

[22] Filed: Jul. 26, 1982

Related U.S. Application Data

[62] Division of Ser. No. 90,156, Oct. 31, 1979, Pat. No. 4,419,360.

[51] Int. Cl.³ .......................................... A01H 43/42
[52] U.S. Cl. ................................... 424/258; 516/165
[58] Field of Search ........................................ 424/258

[56] References Cited
U.S. PATENT DOCUMENTS 3,709,887 1/1973 Cooke et al. ...................... 546/165

Primary Examiner—Paul M. Coughlan, Jr.
Assistant Examiner—D. B. Springer
Attorney, Agent, or Firm—Terence P. Strobaugh

[57] ABSTRACT

This invention relates to compounds and methods of using said compounds of the formula

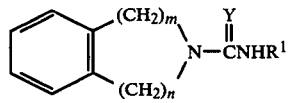

wherein $R^1$ is hydrogen, alkyl, alkenyl or alkoxycarbonylalkyl; Y is O or S; m is an integer of 1 to 3 and n is an integer of 0 to 1 which compounds are insect repellents.

4 Claims, No Drawings

ARTHROPOD REPELLENTS

This is a division of application Ser. No. 090,156 filed Oct. 31, 1979, now U.S. Pat. No. 4,419,360 issued Dec. 6, 1983.

The search for insect repellents which have a combination of excellent repellency, high residual activity and essentially no toxicity is a continuing one due to recognition of the possible toxicity to animals or humans of many known insecticides. Since long lasting repellents avoid these problems with insecticides and provide essentially the same results, compounds having these effects are in great demand.

Accordingly, it is an object of this invention to provide novel methods for repelling arthropods, and also novel compounds and compositions useful in repelling arthropods including stable flies, mosquitoes, ticks and the like.

In accordance with the present invention, there are employed in the compositions for repelling arthropods an active ingredient having the following formula:

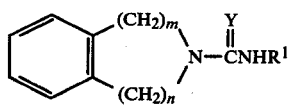

wherein $R^1$ is hydrogen, alkyl, for example, lower alkyl of from 1 to 9 carbon atoms such as methyl, ethyl, n-propyl, n-butyl, sec-butyl, tert-butyl, pentyl, hexyl, heptyl, octyl, nonyl and the like; alkenyl, for example, lower alkenyl of from 2 to 5 carbon atoms such as allyl and the like; or alkoxycarbonyl alkyl, for example, lower alkoxycarbonyl lower alkyl wherein the alkyl or alkoxy have from 1 to 6 carbon atoms wherein lower alkoxy can be methoxy, ethoxy, propoxy, butoxy, pentoxy, and the like and lower alkyl is methyl, ethyl, propyl, butyl, pentyl and the like; Y is O or S; m is an integer of 1 to 3 and n is an integer of 0 to 2.

A preferred embodiment of this invention relates to novel compounds having the following formula:

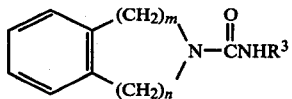

wherein m and n are as defined above; $R^3$ is lower alkyl of from 1 to 5 carbon atoms such as methyl, ethyl, propyl, butyl, pentyl, and the like, lower alkenyl such as allyl and the like or lower alkoxycarbonyl lower alkyl such as methoxycarbonylmethyl, ethoxycarbonylmethyl, ethoxycarbonylethyl, butoxycarbonylethyl and the like. These compounds exhibit particularly good insect repellent and residual action.

Particularly preferred compounds are: N-butyl-1,2,3,4-tetrahydroquinolyl urea, N-propyl-1,2,3,4-tetrahydroquinolyl urea, N-butyl-1,2,3,4-tetrahydroisoquinolyl urea and N-propyl-1,2,3,4-tetrahydroisoquinolyl urea.

The products of this invention are prepared by treating a quinoline or isoquinoline (II, infra) with an appropriately substituted isocyanate (III, infra) at a temperature in the range of from about 0° to about 50° C. in a suitably inert solvent such as benzene, diethyl ether and the like. The following equation illustrates this process:

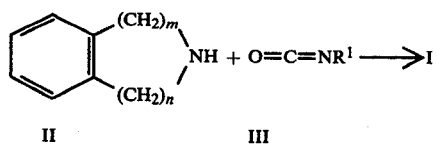

wherein $R^1$, m and n are as defined above.

The compounds of this invention and compositions thereof can be employed over a wide range of concentration in a variety of carriers or diluents conventionally used in the art.

The amount of such compound employed in the insect repellent compositions can vary between from about 0.1 to about 90 weight percent basis of the weight of the composition and will depend upon the intended use. Usually, the compositions contain between about 0.1 to about 10 weight percent of one or more of the compounds, hereinbefore described, and the compound is usually in intimate mixture with the carrier.

When it is desired to use the insect repellent composition directly (i.e., without further dilution), the amount of the compound used can usually vary from between about 0.1 to 5.0 weight percent. When it is desired to formulate a concentrated composition, i.e., one suitable for dilution prior to end use, the compounds will usually be present in the composition in an amount of from about 0.5 to about 90 weight percent.

The carrier employed can be any carrier conventionally used in insect repellent formulations. The carrier should also be one that will not be harmful to the environment. The carrier can be any one of a variety of organic and inorganic liquid, solid, or semi-solid carriers or carrier formulations conventionally used in insect repellent products and can be a mixture of such carriers.

Examples of organic liquid carriers include liquid aliphatic hydrocarbons such as pentane, hexane, heptane, nonane, decane and their analogs, as well as liquid aromatic hydrocarbons. Examples of other liquid hydrocarbons include oils produced by the distillation of coal and the distillation of various types and grades of petrochemical stocks including kerosene oils which are obtained by fractional distillation of petroleum at between 84° C. and 130° C. and which usually have a flash point between 18° C. and 32° C.

Other petroleum oils include those generally referred to in the art as agricultural spray oils which are light and medium spray oils consisting of the middle fractions in the distillation of petroleum and have a viscosity in the range of from about 40 to 85 sec. Saybolt and 4° C. and are only slightly volatile. These oils are usually highly refined and contain only minute amounts of unsaturated compounds as measured by standard sulfonation tests. The customary sulfonation range of such oils is between 90% and 94% of unsulfonatable residue. These oils are paraffin oils and can be emulsified with water and an emulsifier and diluted to lower concentrations and used as sprays. Tall oils obtained from sulfate digestion of wood pulp, like paraffin oils, also can be employed.

In addition to the above-mentioned liquid hydrocarbons, the carrier can contain conventional emulsifying agents (e.g., a non-ionic surfactant such as an ethylene oxide condensate of octyl phenol or an anionic surfactant such as an alkali metal salt of an alkylbenzenesulfonic acid). Such emulsifiers are used to permit the composition to be dispersed in and diluted with water for end use application.

When paraffin oils are employed as carriers in the insect repellent compositions of this invention, they are usually used in conjunction with an emulsifier, the mixture being diluted with water immediately prior to the end-use application. Other suitable paraffin oils, particularly those used with emulsions, are referred to in the art as heavy paraffin oils and usually have a viscosity greater than 85 sec. Saybolt at 4° C.

Other advantageous organic liquid carriers can include liquid terpene hydrocarbons and terpene alcohols such as alpha-pinene, dipentene, terpineol, and the like. Still other liquid carriers include organic solvents such as aliphatic and aromatic alcohols, esters, aldehydes, and ketones. Aliphatic monohydric alcohols include methyl, ethyl, n-propyl, isopropyl, n-butyl, sec-butyl and t-butyl alcohols. Suitable dihydric alcohols include glycols such as ethylene and propylene glycol and the pinacols (alcohols having the empirical formula: $C_6H_{12}(OH)_2$. Suitable polyhydroxy alcohols include glycerol, arabitol, erythritol, sorbitol, and the like. Suitable cyclic alcohols include cyclopentyl and cyclohexyl alcohols.

Conventional aromatic and aliphatic esters, aldehydes and ketones can be employes and are usually used in combination with the above-mentioned alcohols. Still other liquid carriers including high-boiling petroleum products, such as mineral oil and higher alcohols, such as cetyl alcohol can also be employed. Additionally, conventional "stabilizers" or "synergizers" such as t-butyl sulfinyl dimethyl dithiocarbamate, can be employed in conjunction with, or as a component of, the carriers comprising the compositions of this invention.

Solid carriers which can be used in the compositions of this invention include finely divided organic and inorganic solid materials. Suitable finely divided solid inorganic carriers include siliceous minerals such as clay, including bentonite, attapulgite, fuller's earth, diatomaceous earth, kaolin, mica, talc, finely divided quartz, and the like, as well as synthetically prepared siliceous materials, such as silica aerogels and precipitated and fume silicas.

Examples of finely divided solid organic materials include cellulose, sawdust, synthetic organic polymers and the like.

Examples of semi-solid carriers include petroleum jelly, lanolin and the like, and mixtures of liquid and solid carriers which provide semi-solid carrier products.

The above-described compositions can be employed per se or can be diluted with suitable liquids or solids to repel common flying and crawling insect pests, such as roaches, moths, house and stable flies, termites, flour beetles, bean beetles, weevils, ticks, chinch bugs, lice, ants, chiggers, mosquitoes and the like. The compositions, when used to contact an insect environment, effectively repel the insects. By way of example, one advantageous embodiment of a composition of this invention comprises from about 0.1 to about 90 percent, preferably 0.1 to about 10 percent by weight of an active compound falling within the scope of this invention, in intimate mixture with one or more of the above-mentioned carriers.

Insect pests can be repelled by contacting the surfaces on which the insects may slight or crawl with a liquid, solid or semi-solid composition. The contact can be accomplished directly (e.g., by atomizing the composition into the air as a liquid or as a dust so that the material will fall on the desired surface).

By way of further example, insect-infested animals, such as dogs with fleas or poultry with lice, cows with ticks may be treated with the insect repellent compositions by contacting the fur and/or feathers and the lice, fleas and ticks contained therein, thereby ending the insect infestation. Also, granaries and silos can be treated with the compositions of this invention, prior to grain storage, to prevent beetle, weevil, and other insect infestations in the grain to be subsequently stored. Food packaging elements or containers including fiber, cardboard or wooden shipping containers or storage bins, flour sacks, and the like, can be treated with the compositions of this invention to prevent insect infestation.

EXAMPLE 1

N-Butyl 1,2,3,4-Tetrahydroquinolyl Urea

To a 300 ml., 3-necked flask, fitted with a stirrer, condenser and dropping funnel is added a solution of tetrahydroquinoline (13.3 g.; 0.1 mole) in diethyl ether (50 ml.). A solution of n-butyl isocyanate (9.9 g., 0.1 mole) in diethyl ether (10 ml.) is then added dropwise. The reaction mixture is stirred at room temperature for one-half hour. The ether is removed and the residue distilled to afford 20 grams of N-butyl 1,2,3,4-tetrahydroquinolyl urea, b.p. 175°–180° C./1.5 mm.

By following substantially the procedure of Example 1 and by substituting for the tetrahydroquinoline recited therein an equimolar quantity of Compound A and by substituting for the n-butyl isocyanatoacetate recited therein an equimolar quantity of Compound B, the following products are obtained:

| Ex. No. | Compound A | Compound B | Product | Yield |
|---|---|---|---|---|
| 2 | 1, 2, 3, 4-tetra-hydroquinoline | Methyl isocyanate | N—Methyl 1, 2, 3, 4-tetrahydroquinolyl urea, b.p. 160°–165° C./2.0 mm. | 14.5 g. |
| 3 | 1, 2, 3, 4-tetra-hydroquinoline | n-Propyl isocyanate | N—Propyl 1, 2, 3, 4-tetrahydroquinolyl urea, b.p. 165°–170° C./2.0 mm. | 16.0 g. |
| 4 | 1, 2, 3, 4-tetra-hydroquinoline | Ethyl isocyanate | N—Ethyl 1, 2, 3, 4-tetrahydroquinolyl urea, b.p. 165°–167° C./2.0 mm. | 16.0 g. |
| 5 | 1, 2, 3, 4-tetra-hydroquinoline | Allyl isocyanate | N—Allyl 1, 2, 3, 4-tetrahydroquinolyl urea, b.p. 170°–175° C./1.5 mm. | 17.0 g. |
| 6 | 1, 2, 3, 4-tetra- | Ethyl isocyanato- | N—Ethoxycarbonyl | 21 g. |

-continued

| Ex. No. | Compound A | Compound B | Product | Yield |
|---|---|---|---|---|
| | hydroquinoline | acetate | methyl 1, 2, 3, 4-tetrahydroquinolyl urea, b.p. 175°–180° C./1.0 mm. | |
| 7 | 1, 2, 3, 4-tetrahydroquinoline | Hexyl isocyanate | N—Hexyl 1, 2, 3, 4-tetraquinolyl urea | 11.0 g. |
| 8 | 1, 2, 3, 4-tetrahydroquinoline | Octyl isocyanate | N—Octyl 1, 2, 3, 4-tetrahydroquinolyl urea | 13.0 g. |
| 9 | 1, 2, 3, 4-tetrahydroisoquinoline | Methyl isocyanate | N—Methyl-1, 2, 3, 4-tetrahydroisoquinolyl urea, b.p. 185°–190° C./2.0 mm. | 16 g. |
| 10 | 1, 2, 3, 4-tetrahydroisoquinoline | n-Butyl isocyanate | N—Butyl 1, 2, 3, 4-tetrahydroisoquinolyl urea, b.p. 195°–200° C./2.0 mm. | 19.0 g. |
| 11 | 1, 2, 3, 4-tetrahydroisoquinoline | n-Propyl isocyanate | N—Propyl 1, 2, 3, 4-tetrahydroisoquinolyl urea, b.p. 175°–180° C./1.5 mm. | 17.0 g. |
| 12 | 1, 2, 3, 4-tetrahydroisoquinoline | Allyl isocyanate | N—Allyl 1, 2, 3, 4-tetrahydroisoquinolyl urea, m.p. 72°–73° C. | 19.5 g. |
| 13 | 1, 2, 3, 4-tetrahydroisoquinoline | n-Butyl isocyanatoacetate | N—Carboxybutoxymethyl 1, 2, 3, 4-tetrahydroisoquinolyl urea | 24.0 g. |

The following test description and results illustrate the use of the novel compounds of this invention.

Repellency Screen

Male albino guinea pigs (Perfection Breeders) are divided into groups of 2 each and placed into individual cages in a rodent battery equipped with an automatic watering system. Individual animal body weights ranged from 450 to 600 g. Feed and water were provided ad libitum. Guinea pigs are prepared for testing by clipping a patch of hair from the back with a size 10 clipper blade. This permits a residual amount of hair to be left on the animal.

Test compounds are formulated as 5% solutions in acetone. A 2.5 ml. volume of test solution is applied with a medicine dropper pipette to an area on the animal's back measuring approximately 7 cm.×5 cm. This application results in a deposit rate of 3.5 mg./cm². Two guinea pigs are treated with each compound. The test animal is anesthetized with sodium pentobarbital administered intraperitoneally at the rate of 35 mg./kg. and is placed in a cylindrical plastic cage with only the treated portion of the back exposed. The masked animal is introduced into an insect cage filled with either starved stable flies or yellow fever mosquitoes. Approximately 500–1000 insects are used as the challenge. The treated guinea pig is exposed to the test insects for a 5–10 minute period initially and at 3 hours post-treatment and then on a daily basis until the repellency activity of the compound terminates. The residual repellency activity of a compound is regarded as terminated when three or more test insects fed on the guinea pig during the exposure period. N. A. means not active at the test dose.

| | Protection Time | |
|---|---|---|
| Example No. | Stable Fly | Yellow Fever Mosquito |
| 1 | 15 Days (D) | 9 Days (D) |
| 2 | 3 Hours (H) | 1+ D |
| 3 | 13 D | 9 D |
| 4 | 1 D | 2 D |
| 5 | 2 D | 2 D |
| 6 | 3 H | 1 D |
| 9 | 0.5 H | 1 D |
| 10 | 0.5 H | 8 D |
| 11 | 0.5 H | 8 D |
| 12 | NA | 0.5 H |
| 13 | 3 H | 3 H |

What is claimed is:

1. A method for repelling arthropods which comprises applying an effective repellent amount of N-propyl 1,2,3,4-tetrahydroquinolyl urea.

2. A method for repelling arthropods which comprises applying an effective repellent amount of N-butyl 1,2,3,4-tetrahydroisoquinolyl urea.

3. A method for repelling arthropods which comprises applying an effective repellent amount of N-propyl 1,2,3,4-tetrahydroisoquinolyl urea.

4. A method for repelling arthropods which comprises applying an effective repellent amount of N-ethyl 1,2,3,4-tetrahydroquinolyl urea.

* * * * *